(12) United States Patent
Honda et al.

(10) Patent No.: US 8,217,014 B2
(45) Date of Patent: Jul. 10, 2012

(54) PHARMACEUTICAL COMPOSITION FOR TREATMENT OF BLOOD CLOTTING DISORDER

(75) Inventors: Takashi Honda, Nagoya (JP); Junki Takamatsu, Nagoya (JP); Hidenori Toyoda, Nagoya (JP); Koji Yamamoto, Nagoya (JP); Hidemi Goto, Nagoya (JP)

(73) Assignee: National University Corporation Nagoya University, Nagoya-shi (JP)

( * ) Notice: Subject to any disclaimer, the term of this patent is extended or adjusted under 35 U.S.C. 154(b) by 1172 days.

(21) Appl. No.: 11/988,048

(22) PCT Filed: Mar. 9, 2006

(86) PCT No.: PCT/JP2006/304657
§ 371 (c)(1),
(2), (4) Date: Dec. 28, 2007

(87) PCT Pub. No.: WO2007/099652
PCT Pub. Date: Sep. 7, 2007

(65) Prior Publication Data
US 2009/0232769 A1     Sep. 17, 2009

(30) Foreign Application Priority Data
Feb. 28, 2006   (JP) ................................. 2006/053473

(51) Int. Cl.
*A61K 31/505*   (2006.01)
*A61K 31/50*    (2006.01)
(52) U.S. Cl. ............ 514/43; 514/45; 514/46; 514/260.1
(58) Field of Classification Search .................... None
See application file for complete search history.

(56) References Cited

U.S. PATENT DOCUMENTS
2003/0125250 A1   7/2003   Araki et al.

FOREIGN PATENT DOCUMENTS
JP   A-2001-181201   7/2001

OTHER PUBLICATIONS

Yamamoto et al., Anti-HCV agent, ribavirin, elevates the activity of clotting factor VII in patients with hemophilia: a possible mechanism of decreased events of bleeding in patients with hemophilia by ribavirin, Journal of Thrombosis and Haemostasis, 2006, 4:469-70 (first published online Jan. 13, 2006).*
Honda et al., Ribavirin and Use of Clotting Factors in Patients with Hemophilia and Chronic Hepatitis C, JAMA, Mar. 9, 2005, 293(10): 1190-1192.*
Husa, P et al., Treatment of Chronic Hepatitis C in Hemophilic Patients, Acta virologica, 48:35-38 (2004).*
Schulman et al., A randomized study of alpha-interferon plus ribavirin for 6 months or 12 months for the treatment of chronic hepatitis C in patients with bleeding disorders, Haemophilia (2002), 8-129-135.*
Puetz et al., Combination therapy with ribavirin and interferon in a cohort of children with hepatitis C and haemophilia followed at a pediatric haemophilia treatment center, Haemophilia (2004), 10, 87-93.*
Shields et al., Combined alpha interferon and ribavirin for the treatment of hepatitis C in patients with hereditary bleeding disorders, British Journal of Haematology, 108: 254-258 (2000).*
K. Yamamoto et al., "Anti-HCV agent, ribavirin, elevates the activity of clotting factor VII in patients with hemophilia: a possible mechanism of decreased events of bleeding in patients with hemophilia by ribavirin," Journal of Thrombosis and Haemostasis, Jan. 13, 2006, vol. 4, pp. 469-470.
T. Honda et al., "Ribavirin and Use of Clotting Factors in Patients with Hemophilia and Chronic Hepatitis C," JAMA, Mar. 9, 2005, vol. 293, No. 10, pp. 1190-1192.
S. Schulman, "Inhibition of Warfarin Activity by Ribavirin," The Annals of Pharmacotherapy, Jan. 2002, vol. 36, pp. 72-74.
Jun. 13, 2006 International Search Report for related Appln. No. PCT/JP2006/304657.
Dec. 20, 2011 Australian Office Action issued in Australian Patent Application No. 2006339220.
Mar. 27, 2012 Japanese Office Action issued in Japanese Patent Application No. 2008-502635 (with English-language translation).

* cited by examiner

*Primary Examiner* — Sreeni Padmanabhan
*Assistant Examiner* — Svetlana M Ivanova
(74) *Attorney, Agent, or Firm* — Oliff & Berridge, PLC

(57) ABSTRACT

Disclosed is a pharmaceutical composition for the prevention or treatment of blood clotting disorder which can reduce a burden on a patient. The pharmaceutical composition comprises an effective amount of ribavirin or a derivative thereof or a pharmaceutically acceptable salt of ribavirin or the derivative.

16 Claims, 3 Drawing Sheets

SEQUENCE LISTING

<160> NUMBER OF SEQ ID NOS: 6

<210> SEQ ID NO 1
<211> LENGTH: 25
<212> TYPE: DNA
<213> ORGANISM: Artificial Sequence
<220> FEATURE:
<223> OTHER INFORMATION: Primer

<400> SEQUENCE: 1
ttcctggagg agctgcggcc gggct            25

<210> SEQ ID NO 2
<211> LENGTH: 25
<212> TYPE: DNA
<213> ORGANISM: Artificial Sequence
<220> FEATURE:
<223> OTHER INFORMATION: Primer

<400> SEQUENCE: 2
ccgacaggag cgcttggtgc ccgtg            25

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
acacctcgaa agagagtgca tggaa            25

<210> SEQ ID NO 4
<211> LENGTH: 25
<212> TYPE: DNA
<213> ORGANISM: Artificial Sequence
<220> FEATURE:
<223> OTHER INFORMATION: Primer

<400> SEQUENCE: 4
cacaggggta gggccctgtg ggaat            25

<210> SEQ ID NO 5
<211> LENGTH: 25
<212> TYPE: DNA
<213> ORGANISM: Artificial Sequence
<220> FEATURE:
<223> OTHER INFORMATION: Primer

<400> SEQUENCE: 5
tccggcgagc caacaccttc ttgga            25

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
ttgcggcaga aattctcctg taggt            25

PHARMACEUTICAL COMPOSITION FOR TREATMENT OF BLOOD CLOTTING DISORDER

TECHNICAL FIELD

The present invention relates to a pharmaceutical composition that contains an effective dose of a specific nucleoside analog and is used for treating or preventing blood clotting disorders. The invention also pertains to a method of preventing or treating hemorrhage or bleeding of the patient with the blood clotting disorder. The preventing or treating method includes use of the nucleoside analog in the pharmaceutical composition and application of the nucleoside analog to the patient with the blood clotting disorder.

BACKGROUND ART

A purine nucleoside analogue, ribavirin (generic name), is known as an antiviral agent having a wide range of antiviral spectrum.

The blood clotting disorders generally represent blood diseases having hemostatic abnormality and/or coagulation abnormality and include coagulation disorders, platelet disorders, aplastic anemia, and leukemia. The hemostatic abnormality and/or coagulation abnormality of these disorders lead to the bleeding tendency.

For treatment of hemophilia (A or B) as a typical example of the coagulation disorder, replacement therapy is generally performed to supplement the defective or reduced clotting factor. The replacement therapy, however, imposes the heavy physical and economical burdens on the patients and has the relative inconvenience due to the requirement of intravenous injections. The repeated bleeding causes articular disorders. While the risk of virus contamination in transfusion products for replacement therapy has been significantly reduced, there is still a possibility of unknown viral infection like HIV virus infection or hepatitis C virus infection through the blood products in past days. There is also an unsolved problem of expression of an antibody (inhibitor) against the injected factor. Gene therapy to the hemophilia patients has not yet been established.

The hemophilia patients may be required to prevent or treat the HIV virus infection or hepatitis C virus infection due to the use of virus-infected injections. The patient with HIV infection or with virus-induced hepatic disorder may have the blood clotting disorder as the complication due to the decreased coagulation factor or thrombocytopenia.

It has been reported that the combined administration of ribavirin and an interferon decreased the dosage of warfarin as an antithrombotic agent (see Non-Patent Document 1).
Patent Document 1: Japanese Patent Laid-Open No. 2001-181201
Non-Patent Document 1: Shulman A., Ann. Pharmacother. 2002, 36, 72-74

DISCLOSURE OF THE INVENTION

The present invention has an object to provide a pharmaceutical composition for preventing or treating a blood clotting disorder and a corresponding method of preventing or treating the blood clotting disorder, in order to relieve the burden on the patient for prevention or treatment of the blood clotting disorder. The present invention also has another object to provide a pharmaceutical composition for preventing or treating a blood clotting disorder and a corresponding method of preventing or treating the blood clotting disorder, in order to reduce the risk of antibody expression inhibiting prevention or treatment of the blood clotting disorder. The present invention also has another object to provide a pharmaceutical composition for preventing or treating a viral infectious disease accompanied with a blood clotting disorder and a corresponding method of preventing or treating the viral infectious disease accompanied with the blood clotting disorder.

The inventors have found that ribavirin dosing for treatment of chronic hepatitis C surprisingly reduced the bleeding tendency in the patients with hemophilia and chronic hepatitis C during the ribavirin dosing period and after the ribavirin dosing period. It is completely unknown ribavirin has the function of accelerating or improving the blood coagulation in the patients with the blood clotting disorder. The improvement of the blood clotting disorder by ribavirin dosing is beyond expectation in the art. The coagulation improvement by ribavirin dosing is remarkable, although its action mechanism has not been fully elucidated.

According to one aspect, the present invention is directed to a pharmaceutical composition for treating a blood clotting disorder. The pharmaceutical composition contains an effective dose of either a compound expressed by formula (1) or a pharmaceutically acceptable salt of the compound.

[formula (1)]

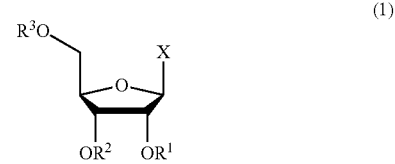

(1)

[in formula (1), each of $R^1$, $R^2$, and $R^3$ independently denotes either H or a substituent, and X is either A or B,
where A represents a group expressed by formula (2) given below:

[formula (2)]

(2)

in formula (2), T denotes either N or C—$R^4$, $R^4$ denotes either H or a substituent, and P denotes either CN or a group expressed by formula (3) given below:
in formula (3), Q denotes one of O, S, and NH, and $R^5$ denotes either H or a substituent, and

[formula (3)]

(3)

B represents a group expressed by formula (4) given below:
in formula (4), V denotes one of O, S and Se, W denotes either CN or a group expressed by formula (5) given below:
in formula (5), Y denotes one of O, S, and NH, and $R^6$ denotes either H or a substituent]

[formula (4)]

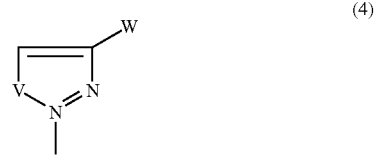

(4)

[formula (5)]

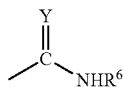

(5)

Preferably $R^1$, $R^2$, and $R^3$ all may denote H. X is preferrably A. in this aspect, in formula (2), $R^4$ is preferably H and in formula (3), Q is O or NH preferably. Further, in formula (3), $R^5$ is preferably H.

Further, the compound is preferably ribavirin and its derivative.

Also, the composition may orally administered and be used for treating clotting factor deficiency preferably. For example, the composition may be used for treating at least either of hemophilia A and hemophilia B.

The compound may have antiviral activity. In this case, the composition may be used for treating a viral infectious disease. Further, the composition may used for treating at least either of HCV-induced and HIV-induced viral infectious diseases. In these cases, the composition may contain an interferon in an effective dose for inhibition of viral activity.

In another aspect, the present invention is directed to use of a compound expressed by formula (1) given above in manufacture of a pharmaceutical composition for relieving or treating a blood clotting disorder:

Also, in another aspect, the present invention is directed to a method of preventing or treating hemorrhage or bleeding of a patient with a blood clotting disorder, administering a compound expressed by formula (1) given above in an effective dose for prevention or treatment of the hemorrhage. In this aspect, when patient with the blood clotting disorder may have a viral infectious disease, the patient may be administered the compound in combination with an interferon in an effective dose for inhibition of viral activity. Also, the viral infectious disease may be at least either of HCV-induced and HIV-induced viral infectious diseases.

Further, in another aspect, the present invention is directed to a pharmaceutical composition for treating hemophilia comprising an effective dose of either of a clotting factor VII or a compound accelerating synthesis of the clotting factor VII or a pharmaceutically acceptable salt thereof. The compound may be expressed by formula (1) given above. The compound is preferably either ribavirin or a ribavirin derivative.

In another aspect, the present invention is directed to a pharmaceutical composition for treating a clotting factor VII-involved blood clotting disorder comprising an effective dose of either a compound expressed by formula (1) given above or a pharmaceutically acceptable salt of the compound. The compound may be either ribavirin or a ribavirin derivative.

BEST MODES OF CARRYING OUT THE INVENTION

Figure 1:
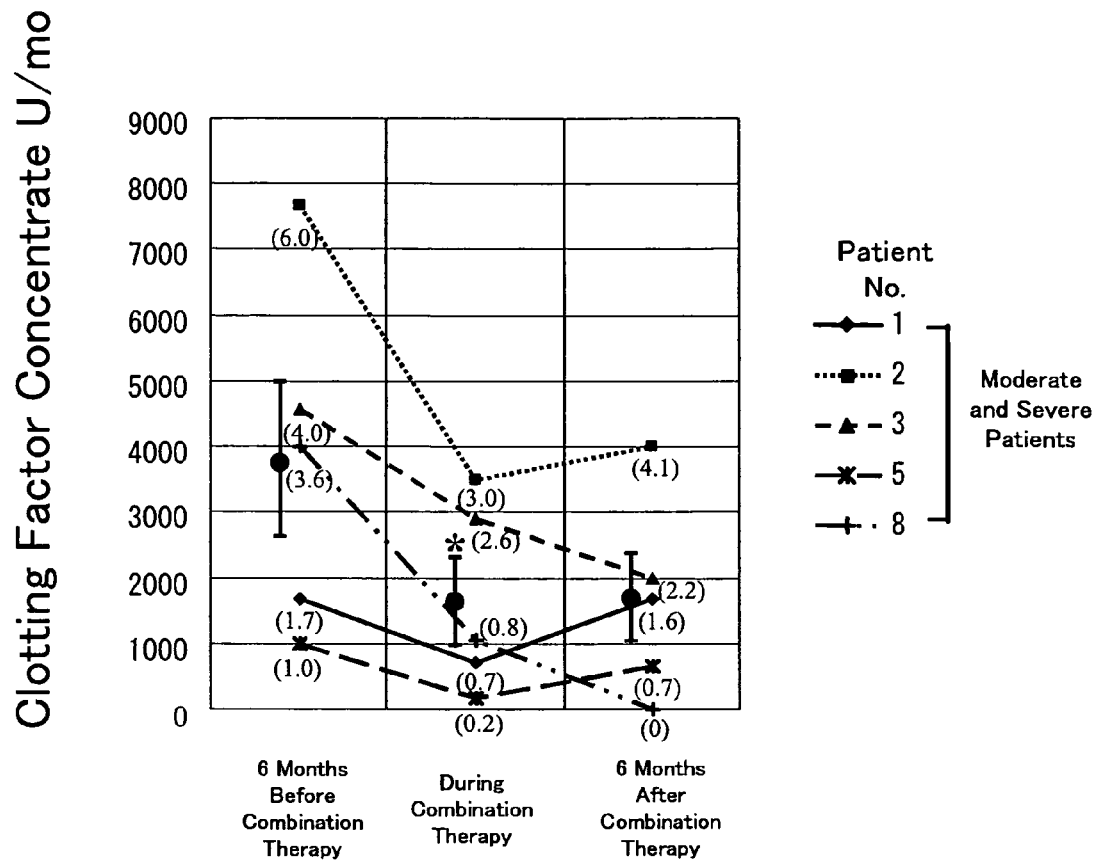
FIG. 1 graphically shows dosing period and changes of monthly average of dose of coagulant before, during and after dosing period of case 1 of Example 1.

Some modes of carrying out the invention are described below in detail.

The pharmaceutical composition for preventing or treating a blood clotting disorder according to one aspect of the invention contains an effective dose of either a compound expressed by formula (1) given below or a pharmaceutically acceptable salt of the compound.

In the compound expressed by formula (1), preferably at least one of $R^1$, $R^2$, and $R^3$ denotes H, and more preferably $R^1$, $R^2$, and $R^3$ are all H. Various substituent groups are applicable for the substituent in $R^1$, $R^2$, and $R^3$, but a carboxy-containing group, for example, $R^7CO-$, is preferable for the substituent. Here $R^7$ may be any of alkyl, acyl, cycloalkyl, heterocyclic, aryl, alkenyl, and alkinyl groups. These groups may be substituted with a hydroxy group or an alkoxy group.

In the compound, X may be either A expressed by formula (2) or B expressed by formula (4) but is preferably A. In A expressed by formula (2), T may be either N or C—$R^4$ (where C is located at the site of T) but is preferably N. In C—$R^4$, $R^4$ denotes either H or a substituent. The substituent in $R^4$ may be any of various substituent groups including alkyl, acyl, cycloalkyl, heterocyclic, aryl, alkenyl, alkinyl, and amino groups. These groups may be substituted with a hydroxy group or an alkoxy group. A preferable example of the substituent is ethynyl (—CCH). $R^4$ is preferably H in general but is preferably $NH_2$ or ethynyl group in some applications.

In A expressed by formula (2), P may be either CN or a group expressed by formula (3) but is preferably the group expressed by formula (3). In the group expressed by formula (3), Q may be any of O, S, and NH but is preferably either O or NH, and $R^5$ denotes either H or a substituent. The substituent in $R^5$ may be any of various substituent groups including alkyl, acyl, cycloalkyl, heterocyclic, aryl, alkenyl, alkinyl, and amino groups. These groups may be substituted with a hydroxy group or an alkoxy group. Any of substituent options 'R' shown in the compounds in [Chemical Expression 22] is also applicable for the substituent in $R^5$. $R^5$ may be $NH_2$ or OH but is preferably H in some applications.

In B expressed by formula (4), V denotes any one of O, S, and Se, and W denotes a group expressed by formula (5). In the group expressed by formula (5), Y may be any one of O, S, and NH but is preferably O, and $R^6$ denotes either H or a substituent. $R^6$ may be $NH_2$ or OH but is preferably H.

In the specification hereof, the respective substituent groups have the following definitions. The alkyl group means linear and branched hydrocarbon chains having 1 to 20 carbon atoms, preferably 1 to 6 carbon atoms, or more preferably 1 to 3 carbon atoms. The alkenyl group means linear and branched hydrocarbon chains having at least one carbon-carbon double bond and 2 to 20 carbon atoms or preferably 2 to 8 carbon atoms. The alkinyl group means linear and branched hydrocarbon chains having at least one carbon-carbon triple bond and 2 to 20 carbon atoms or preferably 2 to 6 carbon atoms. The cycloalkyl group means carbocyclic groups having 3 to 12 carbon atoms, preferably 3 to 7 carbon atoms, or more preferably 3 to 6 carbon atoms that may be substituted with one double bond. The alkoxy group means linear and branched alkyl groups being linked to oxygen and having 1 to 10 carbon atoms. Typical examples of the alkoxy group are methoxy, ethoxy, and tert-butoxy. The aryl group (including aryloxys and aryl moieties of benzyl and other aralkyls) means carbocyclic groups having at least one aromatic ring (for example, phenyl ring) and 6 to 15 carbon atoms, where any of substitutable carbon atoms may be substituted with at least one (for example, one to three) halogen, alkyl, hydroxy, alkoxy, CN, phenoxy, $CF_3$, amino, alkylamino, dialkylamino, SH, S-$M^+$, or —$NO_2$. The aryl group also means polycyclic aromatic rings (for example, quinolyl or isoquinolyl) having at least one hetero atom like N or S. Here $M^+$ represents a cation of an alkaline metal. The aryl alkyl group means the alkyl groups substituted with aryl groups. The acyl group means linear and branched acyl groups having 1 to 20 carbon atoms, preferably 2 to 12 carbon atoms, more preferably 2 to 10 carbon atoms, or most preferably 2 to 6 carbon atoms.

The compound may be, for example, ribavirin (1-β-D-ribofuranosyl-1,2,4-triazole-3-carboxamide) or a ribavirin derivative. Ribavirin and its derivatives are expressed by formula (6) given below:

[formula (6)]

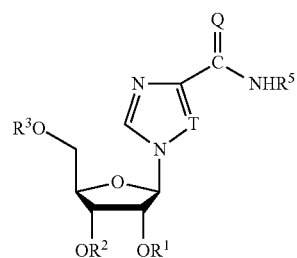

(6)

Ribavirin is the compound having H for all $R^1$ to $R^3$, N for T, O for Q, and H for $R^5$ in formula (6). Ribavirin is preferably used as the compound in the aspect of the invention.

Some examples of the ribavirin derivative are obtained by substituting hydrogen atoms in hydroxyl groups at the sites 2, 3, and 5 in the ribose or by substituting hydrogen atoms in the 1,2,4-triazol groups.

Other examples of the ribavirin derivative include 1-β-D-ribofuranosyl-1,2,4-triazole disclosed in Japanese Patent Laid-Open No. S50-154253, nucleoside derivatives of 1,2,4-triazole-3-carboxamide disclosed in Japanese Patent Laid-Open No. S50-29720, and 1,2,4-triazole nucleoside disclosed in Japanese Patent Laid-Open S53-124271. Various ribavirin derivatives disclosed in Japanese Patent Laid-Open No. 2004-52522 are also applicable to the ribavirin derivative in the aspect of the invention.

Another example of the ribavirin derivative is viramidine having H for all $R^1$ to $R^3$, N for T, NH for Q, and H for $R^5$ in formula (6) (see Antimicrobial Agents and Chemotherapy, May 2004, 1872-1875).

Still another example of the ribavirin derivative is a ribavirin relevant compound AICAR (5-amino-1-β-D-ribofuranosylimidazole-4-carboxamide) (see Virus Research 107(2005), 165-171). AICAR has C—$R^4$ for T, $NH_2$ for $R^4$, and H for $R^5$ in formula (6).

Another example of the ribavirin derivative is 5-ethynyl-1-β-D-ribofuranosylimidazole-4-carboxamide (EICAR). EICAR has C—$R^4$ for T, —CCH (ethynyl group) for $R^4$, and H for $R^5$ in formula (6). The ribavirin derivative may otherwise be any of ribavirin derivatives listed in J. Med. Chem. 1992, 35, 3231-3238.

[EICAR]

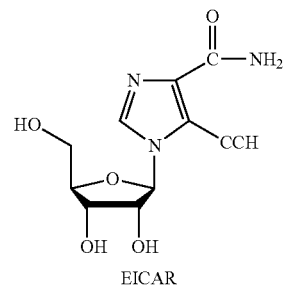

EICAR

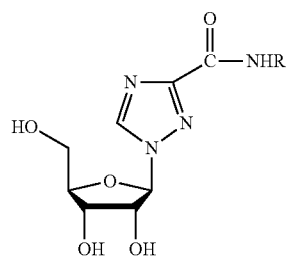

R denotes one of the following;
R = H,
R = —$CH_2CONH_2$,
R = —$CH(CONH_2)$—$CH_2$—$CONH_2$,
R = —$CH(CONH_2)$—$(CH_2)_2$—$CONH_2$,
R = $CH(CONH_2)$—$CH_2$-Phe,
R =
R = $CH_3$

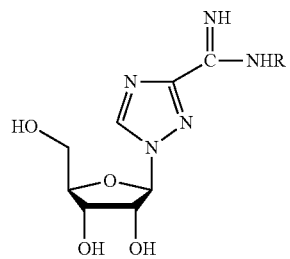

R denotes one of the following;
R = H(HCl),
R = —CN,
R = —$CH_3$(HCl)
R = —$(CH_2)_3$—$CH_3$,
R = —$CH_2$—COOH,
R = —CH(COOH)—$CH_2$—$CONH_2$,
R = —CH(COOH)—$(CH_2)_2$—$CONH_2$
R = —$CH(CONH_2)$—$(CH_2)_2$—$CONH_2$.
R =

The compound may have —$NH_2$ substituted for —$OR^2$ in formula (1). This $NH_2$-substituted compound may have various substituents mentioned previously. Typical example of the $NH_2$-substituted compound include 1-β-D-3'-amino-3'-deoxyribofuranosyl-1,2,4-triazole-3-carboxamide, 1-β-D-3'-amino-3'-deoxyribofuranosyl-1,2,4-triazole-3-carboxyhydrazide, 1-β-D-3'-amino-3'-deoxyribofuranosyl-1,2,4-triazole-3-carbohydroxamic acid, 1-β-D-3'-amino-3'-deoxyribofuranosyl-1,2,4-triazole-5-carboxamide, 1-β-D-3'-amino-3'-deoxyribofuranosyl-1,2,4-triazole-3-carboxamidrazone, 1-β-D-3'-amino-3'-deoxyribofuranosyl-1,2,4-triazole-3-carboxamidoxine (see J. Med. Chem. 1977, 20, 1684-1687).

Some examples of the compound having B in formula (1) other than the ribavirin derivatives include selenazofurin (2-β-D-ribofuranosylselenazole-4-carboxamide), thiazofurin (2-β-D-ribofuranosylthiazole-4-carboxamide) (see Virus Research 107 (2005), 165-171).

Another example of the compound having B in formula (1) is oxazofurin (2-β-D-ribofuranosyloxazole-4-carboxamide) (see J. Med. Chem. 1990, 33, 2849-2852).

Other derivatives available for the compound include selenophenfurin, furanfurin, and imidazofurin (see Bioorganic & Medical Chemistry Letters 11 (2001) 67-69).

Another available example is ara-thiazofurin (2-β-D-arabinofuranosylthiazole-4-carboxamide, Ara-T) (see J. Med. Chem. 1988, 31, 1026-1031).

Other available examples include 1-(2'-deoxy-β-D-ribofuranosyl)-3-nitropyrrole, 1-β-D-ribofuranosyl-3-nitropyrrole, and 3-NPNTP (see Biochemistry 2002, 41, 9026-9033).

The contents of the patent documents and the patent application laid-open cited in the specification hereof, especially the general formula and the compounds described and mentioned therein, are fully incorporated in the specification hereof for the purpose of reference.

The applicability of the individual compounds for the pharmaceutical composition of the invention is readily specified by evaluating their effects and efficacies, toxicities, absorption, metabolism, and pharmacokinetic features and characteristics according to the methods disclosed in the specification hereof or the cited and other references as well as according to the common knowledge in the art.

These compounds preferably have antiviral activities against various viruses, for example, respiratory infection viruses, such as influenza virus, hemorrhagic fever with renal syndrome (HFRS) virus, herpes virus, Lassa virus, measles virus, AIDS virus (HIV virus), hepatitis C virus, and hepatitis B virus. For example, single dosing of ribavirin has the antiviral activity against BVDV, which is related hepatitis C virus. The antiviral activity against each target virus is measured and evaluated according to any of known appropriate methods.

The nucleoside derivative, for example, ribavirin, included in the pharmaceutical composition of the invention is used to systemically or preferably orally alleviate or treat the blood clotting disorder, or more specifically to prevent hemorrhage or bleeding and accelerate hemostasis of the patient with the blood clotting disorder.

The nucleoside derivative of the invention is effective and efficacious for blood clotting disorders, that is, various blood diseases with hemostatic or clotting disorders. Typical examples of the blood clotting disorder include coagulation disorders like hemophilia A, hemophilia B, von Willebrand disease, disseminated intravascular coagulation (DIC), and vitamin K deficiency, platelet disorders like Bernard-Soulier syndrome, Glanzmann's disease (thrombasthenia), thrombocytopenia, platelet dysfunction, disseminated intravascular coagulation (DIC), thrombotic thrombocytopenic purpura (TTP), hemolytic uremic syndrome (HUS), idiopathic thrombocytopenic purpura (ITP), Kasabach-Merritt syndrome, and Henoch-Schonlein purpura (HSP), aplastic anemia, leukemia, pernicious anemia, sideroblastic anemia, Wiskott-Aldrich syndrome, chronic myeloproliferative disorder, afibrinogenemia, antithrombin III deficiency, protein C deficiency, protein S deficiency, antiphospholipid antibody syndrome (APS), and dysfibrinogenemia. Other examples are bleeding disorders like HIV-induced thrombopenia and coagulation factor deficiency as well as thrombopenia and coagulation factor deficiency accompanied with hepatic disorders, hepatitis, and cirrhosis induced by hepatitis viruses, various other viruses, and any other causes.

The nucleoside derivative, typically ribavirin, has the function of accelerating synthesis of the coagulation factor VII. As described clearly in Examples below, administration of ribavirin effectively reduces the bleeding tendency of the patients with hemophilia A or hemophilia B, in combination with the increased coagulation factor VII in the plasma. Namely the coagulation factor VII is the active ingredient of the pharmaceutical composition for treating hemophilia. The coagulation factor VII is biosynthesized in liver cells in a vitamin K dependent manner and is a serine proteolytic enzyme precursor circulated in blood as a single-strand glycoprotein having the molecular weight of 50 KDa. The compounds accelerating synthesis of the coagulation factor VII and their pharmaceutically acceptable salts like the nucleoside derivative of the invention are usable for the pharmaceutical composition for treating hemophilia. The coagulation factor VII is biosynthesized in liver cells in the vitamin K-dependent manner. It is accordingly preferable that vitamin K is used as an ingredient of the pharmaceutical composition or in combination with the pharmaceutical composition.

The nucleoside derivative of the invention, such as ribavirin, accelerate synthesis of the coagulation factor VII and is accordingly usable for the pharmaceutical composition for treating coagulation factor VII-related blood clotting disorders, for example, congenital coagulation factor VII deficiency. Namely ribavirin or the nucleoside derivative of the invention may be used as the alternative of the coagulation factor VII or the coagulation factor VII preparation. The nucleoside derivative may be used as an ingredient of the coagulation factor VII preparation or in combination with the coagulation factor VII preparation.

In administration of the nucleoside derivative for accelerating biosynthesis of the coagulation factor VII or as the coagulation factor VII preparation, its dosage and administration can follow the dosage and administration of the pharmaceutical composition for treating the blood clotting disorder described later. The adequate dosage of the nucleoside derivative may be determined according to the synthesis of the coagulation factor VII in the plasma.

The nucleoside derivative having appropriate antiviral activity is effective for viral infectious diseases, especially hepatitis C virus infection. The viral infectious diseases include a wide range of RNA virus and DNA virus infections. The RNA virus and the DNA virus are not restrictive but may be, for example, flavivirus (including flavivirus genus, pestivirus (including Kunjin virus), hepadnavirus (including hepatitis B virus), flavividae (including dengue virus and chronic hepatitis C virus), and arbovirus (including West Nile virus)), orthomyxovirus, paramyxovirus, arenavirus, bunyavirus, herpes virus, adenovirus, pox virus, and retrovirus.

Typical examples of the viral infectious disease include influenza A virus infection, influenza B virus infection, parainfluenza virus infection, RS virus (RSV) infections (for example, RSV bronchiolitis, RSV pneumonia, especially infant and childhood RSV infections and RSV pneumonia in the patients with cardiopulmonary disorders), measles virus infection, Lassa fever virus infection, Korean hemorrhagic fever virus infection, hepatitis B virus (HBV) infection, Crimean-Congo hemorrhagic fever virus infection, HCV infection, HIV infection, encephalitis and Saint Louise encephalitis induced by West Nile virus or Kunjin virus, and virus infections in the patients with immune disorders.

The concentration of ribavirin required for in-vitro inhibition of the viral infectious disease is disclosed in Goodman & Gilman's 'The Pharmacological Bases of Therapeutics', $9^{th}$ edition (1996), McGraw Hill, NY, 1214-1215 pages. As information on the Virazole product, 18-hour exposure of Virazole aerosol at the dosage of 20 mg/ml is disclosed in 1999 Physicians Desk Reference, 1382-1384 pages.

The dosage and the medication cure procedure of ribavirin are also disclosed in Chapter 2-2 (126-130 pages) of Sidewell, R. W. et al., Pharmacol. Ther. 1979 Vol. 6, pp 123-146. The dosage and dose regimen for oral and parenteral administration and aerosol administration of ribavirin in various preclinical and clinical researches and studies are disclosed in 4-9 pages of Fernandes, H. et al., Eur. J. Epidemiol., 1986, Vol 2(1) pp 1-14.

In the use of the nucleoside derivative for treating the blood clotting disorder or the viral infection, such as the HCV-induced hepatitis C or the HIV-induced acquired immune deficiency syndrome, the nucleoside derivative may be administered simultaneously with an interferon or may be mixed in advance with an interferon as the ingredients of the pharmaceutical composition for the simultaneous administration. Such drug formulation or administration is extremely effective for ribavirin or the nucleoside derivative having antiviral activity.

The interferon administrated simultaneously or in combination with the nucleoside derivative may be an interferon α. Here the interferon α represents an extremely homogeneous, species-specific protein family that interferes with viral replication and cell proliferation and regulates the immune response. Although not restrictive, preferable examples of the interferon α include recombinant interferon α-2b, such as Intron-A available from Schering-Plough Corporation, Kenilworth, N.J., recombinant interferon α-2a, such as Roferon available from Hoffmann-La Roche, Nutley, N.J., recombinant interferon α-2c, such as Berofor available from Boehringer Ingelheim Pharmaceuticals Inc., Ridgefield, Conn., interferon α-n1 as the natural interferon α-purified mixture, such as Sumiferon available from Dainippon Sumitomo Pharma Co. Ltd., Japan, interferon α-n1 (INS), such as Wellferon available from Glaxo-Wellcome Ltd., London, UK, consensus interferon α disclosed in U.S. Pat. Nos. 4,897,471 and 4,695,623 (especially Examples 7, 8, and 9), specific products available from Amgen Inc., Newbury Park, Calif., interferon α-n3 as the natural interferon α mixture, such as Alferon manufactured by Interferon Sciences and available from Purdue Frederick Co., Norwalk, Conn., interferon α-2a, and interferon α-2b. Among all these interferons, interferon α-2b is widely approved for treatment of chronic hepatitis C in the world and is thus most preferable. The manufacture of interferon α-2b is described in U.S. Pat. No. 4,530,901.

The interferon may be modified adequately. A typical example of the modified interferon is a PEGylated interferon. The PEGylated interferon represents polyethylene glycol-modified conjugate of interferon α, preferably interferon α-2a or interferon α-2b. A preferable example of the polyethylene glycol-modified interferon α-2b conjugate is $PEG_{12000}$-interferon α-2b. This PEGylated interferon is manufactured by, for example, the method disclosed in International Publication WO95/13090 and is the conjugate having urethane bond between the amino group of interferon α-2a or interferon α-2b and the polyethylene glycol having the mean molecular weight of 12000.

The pharmaceutical composition including the nucleoside derivative may be administered orally or parenterally (for example, subcutaneous (SC), intramuscular (IM), intravenous (IV), or intraperitoneal (IP)). The pharmaceutically composition may otherwise be administered locally, intravaginally, or by inhalation (oral or intranasal). Oral administration of the pharmaceutical composition is preferable.

An equivalent amount of the nucleoside derivative or its pharmaceutically acceptable salt may be administered with any appropriate pharmaceutically acceptable (solid or liquid) inactive carrier or diluent. The pharmaceutically acceptable salt is selected among various known salts but is preferably trifluoroacetate, tosylate, mesylate, or chloride.

Solid preparation of the pharmaceutical composition including the nucleoside derivative may be powder, tablet, granule, capsule or cachet, or suppository. The powder or tablet preparation may contain an active ingredient in a range of about 5 to 95%. The appropriate solid carrier is known in the art and is, for example, magnesium carbonate, magnesium stearate, talc, sugar, or lactose. The solid preparations of capsule, powder, cachet and capsule are suitable for oral administration. The manufacturing methods of various pharmaceutically acceptable carriers and compositions are described in A. Gennaro (ed.), Remington's Pharmaceutical Sciences, $18^{th}$ edition (1990), Mack Publishing Col, Eaton, Pa.

Liquid preparation of the pharmaceutical composition including the nucleoside derivative may be solution, suspension, or emulsion. Typical examples are aqueous solutions and water-polyethylene glycol solutions for parenteral injection. The parenteral preparation for intravenous, intramuscular, or subcutaneous injection is generally a sterilized solution and may include a regulator (salt or glucose) and a buffer. The orally administered solution, suspension, or emulsion may be turbid. Another example of the liquid preparation is a solution for intranasal administration. Aerosol preparation suitable for inhalation includes the powder or liquid pharmaceutical composition and may be administered in combination with a pharmaceutically acceptable carrier like an inactive gas (for example, nitrogen). The solid preparation of the pharmaceutical composition may be changed to a liquid preparation immediately before its oral or parenteral administration. Such liquid preparation may be solution, suspension, or emulsion. The nucleoside derivative may be delivered transdermally. The transdermal delivery may be in the form of cream, lotion, aerosol, or emulsion. The transdermal delivery may be attained by means of skin patch in a matrix or reservoir form generally used in the field.

The pharmaceutical composition of the invention is preferably formulated to be suitable for single-dose. The preparation may be divided in appropriate unit dose containing an appropriate dose (effective dose for a desired target) of the active ingredient.

The effective dose of the nucleoside derivative included in the pharmaceutical composition of the invention depends upon the target disorder or disease, the compound used, the age, the weight, and the symptoms of the patient, the administration form, and the type and the dosage of the interferon that may be used in combination. For example, in oral administration to the adult patient, ribavirin is administered once to several times per day with the daily dose of preferably in a range of about 1 mg/kg to 200 mg/kg, more preferably in a range of about 1 mg/kg to 100 mg/kg, or most preferably in a range of about 2 mg/kg to 40 mg/kg. The appropriate dosage and administration of the nucleoside derivative in specific conditions may be determined according to the common knowledge in the art, when necessary.

The pharmaceutical composition of the invention including the nucleoside derivative may be administered to prevent or treat bleeding of the patient with the blood clotting disorder. Administration of the pharmaceutical composition of the invention for a certain time period significantly reduces the bleeding tendency of the patient with the blood clotting disorder even in the presence of some non-dosing period. A dosing period and a non-dosing period may thus be combined adequately in administration of the pharmaceutical composition to the patient with the blood clotting disorder.

The nucleoside derivative may be administered simultaneously or in combination with the interferon to the patient with the viral infectious disease, especially the HIV-infected or HCV-infected patient, as mentioned previously. The administration and formulation form of the pharmaceutical composition including and activating both the nucleoside derivative and the interferon may be transdermal, suppository, sustained-release, or lung inhalation. Oral administration of the interferon α, especially PEGylated interferon α, is not effective. The interferon α is accordingly administered in a parenteral manner, preferably by subcutaneous (SC), intravenous (IV), or intramuscular (IM) injection. Parenteral administration of the interferon is thus preferably combined with the pharmaceutical composition of the invention including the nucleoside derivative. In combined administration of the pharmaceutical composition of the invention including the nucleoside derivative with the interferon, the pharmaceutical composition may be administered orally as capsule, tablet, or liquid or intranasally as aerosol spray, while the interferon may be administered parenterally by SC, IV, or IM injection.

The effective dose of the interferon depends upon the target disorder or disease, the compound used, the age, the weight, and the symptoms of the patient, the administration form, and the type and the dosage of the nucleoside derivative used in combination. For example, the interferon may be administered once to several times per week with the weekly dose in a range of about 1 million to 100 million international units (IU), preferably in a range of about 1 million to 70 million IU, or more preferably in a range of about 1 million to 10 million IU. The appropriate dosage and administration of the interferon in specific conditions may be determined according to the common knowledge in the art, when necessary. The effective dose of the PEGylated interferon depends upon the target disorder or disease, the compound used, the age, the weight, and the symptoms of the patient, the administration form, and the type and the dosage of the nucleoside derivative used in combination. For example, PEGylated interferon α-2b may be administered once to several times per week with the weekly dose in a range of about 0.1 to 100 μg/kg, preferably in a range of about 0.1 to 10 μg/kg, or more preferably in a range of about 0.1 to 3.0 μg/kg. The appropriate dosage and administration of the peginterferon in specific conditions may be determined according to the common knowledge in the art, when necessary.

In combined use of the nucleoside derivative and the interferon, the single dosing period of the nucleoside derivative, the combined dosing period of the nucleoside derivative and the interferon, the single dosing period of the interferon, and their administration forms are appropriately set by the person who actually treats the patient.

EXAMPLES

Some examples of administration are described below, although they are not restrictive in any sense but only illustrate the pharmaceutical composition according to the aspect of the invention.

Example 1

Administration Example 1

(Drug Administration)

Ribavirin (available as the trade name 'Rebetol' from Schering-Plough Corporation) and interferon α-2b (available as the trade name 'Intron A' from Schering-Plough Corporation) were used respectively as the nucleoside derivative and the interferon of the invention. Ribavirin was orally administered, while the interferon was intravenously administered.

These medicines were administered to the HCV-positive patients with hemophilia shown in Table 1. Interferon α-2b alone was administered to the patients Nos. 1, 2, 3, and 5, prior to the combined administration of this Example 1. In the interferon single dosing period, the interferon was administered to the patients Nos. 1, 2, 3, and 5 every day with the dosage of 6 MU (million units) per day for the first 2 weeks and 3 times per week for the subsequent 22 weeks. HCV was not eliminated in this interferon single dosing period. In the combined administration of this Example 1, Intron A was administered to all the patients every day with the dosage of 6 MU per day for the first 2 weeks and 3 times per week for the subsequent 22 weeks. Ribavirin was orally administered with the dosage of 600 mg/day to the patients having the weight of less than 60 kg and with the dosage of 800 mg/day to the patients having the weight of not less than 60 kg. The dosage of ribavirin was reduced by 200 mg/day to the patients having the hemoglobin content of blood decreasing to or below 10 g/dl due to hemolytic anemia.

TABLE 1

| Patient No. | Age | Hemophilia Type | Severity | Duration, y | HCV-RNA level, kIU/ml | HCV Genotype | Duration of HCV infection, y | Ribavirin Load, mg/d | Eradication of HCV |
|---|---|---|---|---|---|---|---|---|---|
| 1 | 28 | A | Moderate | 28 | 44 | 3a | 27 | 800 | YES |
| 2 | 61 | A | Severe | 61 | 640 | 3a | 29 | 800 | YES |
| 3 | 50 | A | Severe | 50 | 850 | 1b | 34 | 600/400 | NO |
| 4 | 42 | B | Mild | 42 | 510 | 2a + 1b | 30 | 800 | YES |
| 5 | 44 | A | Severe | 44 | 600 | 3a | 26 | 800 | YES |
| 6 | 52 | A | Mild | 52 | 750 | 2b | 22 | 600 | YES |
| 7 | 37 | A | Mild | 37 | 59 | 1a | 29 | 800/600 | NO |
| 8 | 44 | B | Moderate | 44 | 310 | 1a | 33 | 800 | YES |

The HIV infection status was detected with an HIV antibody in Particle Agglutination Assay (Fujirebio Inc).

All the patients except the patient No. 7 were HIV negative.

The severity of hemophilia was mild for the coagulation activity of over 5%, moderate for the coagulation activity of 1 to 5%, and severe for the coagulation activity of below 1%.

The HCV-RNA level was measured at the start of treatment with Amplicor HCV Assay, version 2.0 (Roche Diagnostic Systems).

The gene type of the HCV virus was determined according to the base sequence in the 5'-UTR region.

Eradication of HCV was considered positive when the absence of serum HCVRNA was maintained for 24 weeks after the treatment was completed. The patient No. 3 had ribavirin administration with the dosage of 600 mg/day for the first 12 weeks and with the dosage of 400 mg/day for the subsequent period.

The patient No. 7 had ribavirin administration with the dosage of 800 mg/day for the first 8 weeks and with the dosage of 600 mg/day for the subsequent period.

The use of clotting factors was assessed by patient logs. The clotting factors are generally not used for patients with mild hemophilia. The doses (mean value) of the clotting factors before the combined dosing period of this Example 1, during the combined dosing period, and after the combined dosing period were evaluated. A significant difference at P<0.05 was evaluated by (paired) t-test. Ability to perform activities of daily living was assessed by interview. The results of evaluation are shown in Table 2 and FIG. 1.

TABLE 2

| Patient No. | Age | Hemophilia Type | Severity | Times of Bleeding Requiring Treatment (Before, During, After Thrapy) | | |
|---|---|---|---|---|---|---|
| 1 | 28 | A | Moderate | 1.7 | 0.7 | 1.6 |
| 2 | 61 | A | Severe | 6.0 | 3.0 | 4.1 |
| 3 | 50 | A | Severe | 4.0 | 2.6 | 2.2 |
| 5 | 44 | A | Severe | 1.0 | 0.2 | 0.7 |
| 8 | 44 | B | Moderate | 3.6 | 0.8 | 0.0 |

As shown in Table 2 and FIG. 1, with regard to the 5 patients with moderate or severe hemophilia requiring the use of the clotting factors, the monthly mean dosage of the clotting factors were 3783 U (standard deviation: 2646) in the 6 month-period before the combined dosing period, was 1605 U (standard deviation: 1488) in the combined dosing period, and was 1667 U (standard deviation: 1528) in the 6-month period after the combined dosing period. The monthly mean dosage in the combined dosing period was remarkably lower than the monthly mean dosage in the 6-month period before the combined dosing period (P<0.03). The monthly mean dosage in the 6-month period after the combined dosing period was still significantly lower than the monthly mean dosage in the 6-month period before the combined dosing period (P<0.06). The monthly mean bleeding frequency to be treated with the clotting factors for these 5 patients is shown in Table 2. The cause of bleeding was mainly hemorrhagic arthropathy and was partly mucosal hemorrhage or intramuscular hemorrhage.

As clearly understood from these results, the dosage and the administration frequency of the clotting factors were significantly reduced in the combined dosing period of ribavirin and the interferon. This means reduction of the bleeding tendency. With regard to the patients Nos. 1, 2, 3, and 5 having administration of the interferon alone before the combined dosing period, the bleeding tendency was significantly reduced in the combined dosing period, compared with that in the interferon single dosing period. The reduction of the bleeding tendency is thus assumed as the effect of ribavirin alone. No such reduction of the bleeding tendency was observed by the single interferon dosing to the 47 hemophilia patients with hepatitis C including these 4 patients as the subjects of the combined dosing. This result supports the assumption.

With regard to 2 patients out of these 4 patients, the dosage of the clotting factors was further reduced in the 6-month period after the combined dosing period. The reduced bleeding tendency naturally improves the physical activity in the combined dosing period. This may lead to muscle development and prevent amyotrophy caused by hemarthrosis. The muscle development may lower the stress on joints and reduce the potential of the spontaneous hemorrhagic arthropathy.

According to these experimental results, single dosing of the nucleoside derivative, such as ribavirin, or the combined dosing of ribavirin with the interferon is expected to significantly reduce the dosage and the administration frequency of the clotting factors to the hemophilia patients and lower the bleeding tendency of these patients. This desirably lessens the various burdens on the patients, while eliminating or at least reducing the risk of viral infection and the inhibition of the treatment efficacy by the appearance of an inhibitor in replacement therapy. The combined administration of ribavirin and the interferon also enables treatment of the viral infectious disease, for example, by eliminating the HCV virus from the hemophilia patients with hepatitis C, and remarkably improves the quality of life (QOL) of the patients. The decreased dosage of the clotting factors desirably saves the high medical expenses.

Example 2

Administration Example 2

(Drug Administration)

The medicines used in this Example 2 were ribavirin (trade name: Rebetol) and interferon α-2b (trade name: Intron A) identical with those in Administration Example 1. These medicines were administered to 9 hemophilia patients under anti-HCV combined treatment. Among the 9 hemophilia patients (age: average±SD: 42.5±10.4), 7 patients had hemophilia A and 2 patients had hemophilia B. According to the liver biopsy prior to the combined dosing, all the patients did not have hepatic cirrhosis but had chronic hepatitis. In the 24-week combined dosing period, interferon α-2b and ribavirin (600 mg to 800 mg per day) were administered to these 9 patients with the same dosages as those in Administration Example 1.

(Measurement of Coagulation Factors VII and X)

The coagulation activity of the coagulation factor VII in the plasma was measured for these patients before the start of the combined dosing and 4 weeks after the start of the combined dosing. The results of the measurement are shown in Table 3 and FIG. 2.

TABLE 3

| | Before Start of Therapy | After Start of Therapy | Increase Rate |
|---|---|---|---|
| Factor FII Clotting Activety | 86.3 ± 7.6% | 102.0 ± 10.3% | 15.7 ± 8.8% |

Figure 2:
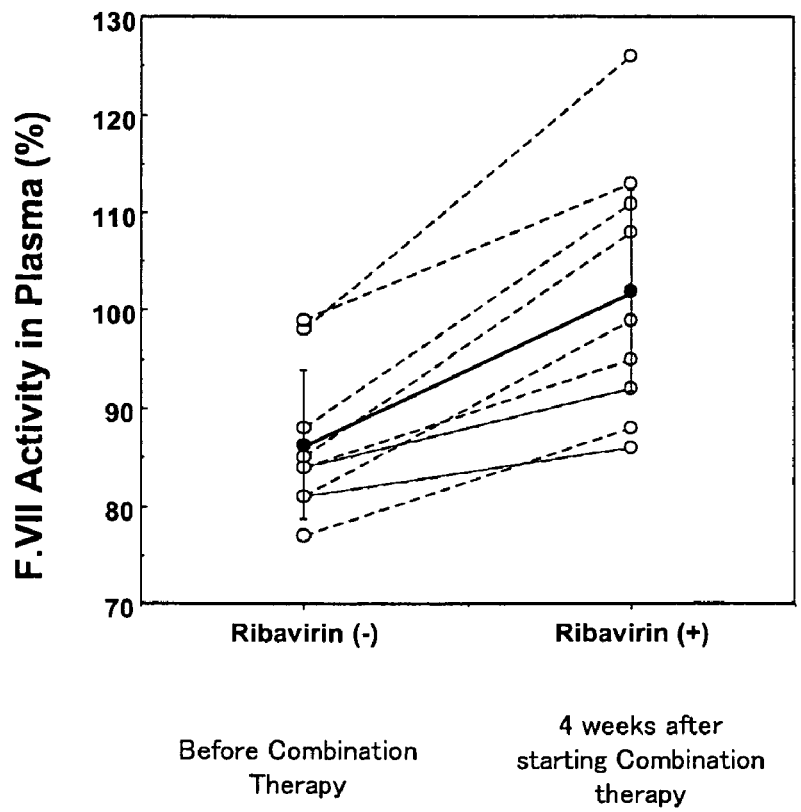
FIG. 2 shows analysis results of Factor VII's clotting activities in blood plasma of nine patients before start dosing period and four weeks after start in case 2 of Example 2. Each circle outline with blank inside shows individual data before and after start of dosing period and each dotted line is formed with connecting data of identical patient. Each black circle and error bar shows average and standard deviation, respectively.

As shown in Table 3 and FIG. 2, the coagulation activity of the coagulation factor VII in the plasma was increased for all the patients 4 weeks after the start of the combined dosing, compared with that before the start of the combined dosing (average: 15.7%±8.8% (maximum: 28%, minimum: 5%), p<0.04 relative to the activity before start of ribavirin dosing). The increased coagulation activity of the coagulation factor VII was independent of the improvement tendency of the separately measured hepatic functions (albumin, total bilirubin, and cholinesterase) of the patients during the combined dosing period. No significant increase of the coagulation activity (5%, 8%) was found in 2 of the 9 hemophilia patients (one patient: HIV positive, the other patient: hepatitis C virus and hepatitis B virus positive). The activated coagulation factor VII (FVIIa) in the plasma was measured with Staclot VIIa-rTF (Diagnostica Stago, Asnieres, France) before the start of the combined dosing and 4 weeks after the start of the combined dosing. The measurement result showed a significant increase (25.3±14.8 mU/ml) of the activated coagulation factor VII. This well agreed with the increasing tendency of the coagulation factor VII. The similar measurement was performed for the coagulation factor X in the plasma. No significant change in coagulation activity of the coagulation factor X was observed before and after the start of the combined dosing (data is not specifically shown here). According to these experimental results, the increased coagulation activity of the coagulation factor VII after the start of the combined dosing is consistent with the reduced bleeding tendency by ribavirin administration in Administration Example 1 (warfarin resistance). It is thus assumed that the increased coagulation activity of the coagulation factor VII leads to the reduced bleeding tendency.

Example 3

Figure 3:
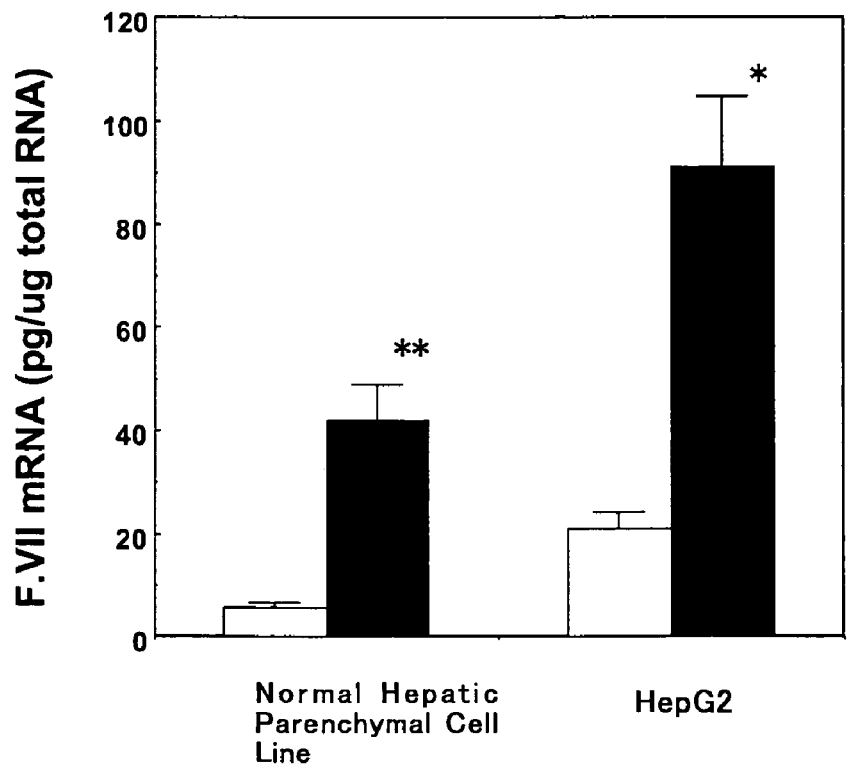
FIG. 3 graphically shows results of expression analysis of Factor VII of Example 3. A white bar and a black bar show culture with and without ribavirin, respectively (*$p<0.02$, **$p<0.01$).

Analysis of Gene Expression of Coagulation Factor VII and Other Relevant Factors in Cell Culture Line In the presence of interferon α-2b (0.75 µg/ml), the gene expression levels of the coagulation factors VII and X and prothrombin were measured in the hepatic parenchymal cell line (Cambrex Bio Science Walkersville Inc., Walkersville, Md., USA) cultured at the clinical ribavirin concentration (150 µg/ml) or in the human hepatocellular liver carcinoma cell line or HepG2 cell line (ATCC, Manassas, Va., USA). The mRNA expression levels of the coagulation factors VII and X and prothrombin were measured according to the protocols of real-time quantitative RT-PCR with ABI Prism 7700 Sequence Detection (Perkin Elmer Biosystems, Foster City, Calif., USA) and SYBR Green PCR kit (Perkin Elmer Biosystems). The real-time quantitative RT-PCR was repeated twice. The following primary pairs were used for determination of the mRNA of the genes. The results of analysis of the mRNA expression level of the coagulation factor VII are shown in FIG. 3.

```
[Clotting Factor VII]
primer (F):
                                            (SEQ ID NO: 1)
-ttc ctg gag gagctg cgg ccgggc t-(25 bp: 241-265)

primer (R):
                                            (SEQ ID NO: 2)
-ccg aca ggagcg ctt ggtgcc cgt g-(25 bp: 546-570)

[Clotting Factor X]
primer (F):
                                            (SEQ ID NO: 3)
-aca cct cgaaag aga gtgcat gga a-(25 bp: 178-202)

primer (R):
                                            (SEQ ID NO: 4)
-cac agg ggtagg gcc ctgtgg gaa t-(25 bp: 518-542

[Prothrombin]
primer (F):
                                            (SEQ ID NO: 5)
-tcc ggc gag ccaaca cct tcttgg a-(25 bp: 153-177)

primer (R):
                                            (SEQ ID NO: 6)
-ttg cgg cagaaa ttc tcctgt agg t-(25 bp: 483-507)
```

As shown in FIG. 3, significant mRNA inductions of the coagulation factor VII were observed both in the normal hepatic parenchymal cell line and in the HepG2 cell line 48 hours after start of the ribavirin dosing (about 4 times: p<0.01, about 3 times: p<0.02). No significant induction was, however, observed for the coagulation factor X or prothrombin (data are not specifically shown). According to these experimental results, it is assumed that the reduced bleeding tendency by ribavirin dosing is ascribed to the accelerated gene expression of the coagulation factor VII.

Example 4

Administration Example 3

The variations in coagulation activities of the coagulation factors in the plasma were evaluated in the combined administration of ribavirin and the interferon to the chronic hepatitis C patients with or without hemophilia.

The medicines used in this Example 4 were ribavirin (trade name: Rebetol) and interferon α-2b (trade name: Intron A) identical with those in Administration Example 1. These medicines were administered to the hepatitis patients under anti-HCV combined treatment as shown in Table 4 for a 48-week period. Of these patients, 9 patients were with hemophilia and 27 hepatitis patients were without hemophilia. Pegintron was administered to all the patients once a week with the dosage of 1.5 µg/Kg for 48 weeks, whereas Rebetol was simultaneously administered to the 9 hemophilia patients with the dosage of Administration Example 1 (600 mg to 800 mg per day).

TABLE 4

|  | Hemophilia Group n = 9 | Non-Hemophilia Group n = 27 |
|---|---|---|
| Age | 40.9 ± 9.9 | 57.5 ± 9.7 |
| Male/Female | 9/0 | 18/9 |
| ALT (IU/L) | 96.3 ± 94.9 | 77.7 ± 39.7 |
| PLT (IU/L) | 16.6 ± 5.6 | 14.7 ± 4.0 |

(Measurement of Coagulation Activities of Coagulation Factors VII and X and Prothrombin)

The prothrombin time (PT) in the plasma was measured for the patients before the start of the dosing and 12 weeks after the start of the dosing, for the purpose of evaluation of the coagulation activity. The results of the measurement are shown in Table 5.

TABLE 5

|  | PT Before Therapy | PT After Therapy | Increase Rate |
|---|---|---|---|
| Hemophilia Group | 90.0 ± 12.2% | 99.4 ± 14.3% | 9.4 ± 8.4% |
| Non-Hemophilia Group | 94.9 ± 14.4% | 100.0 ± 16.8% | 5.4 ± 12.6% |

As shown in Table 5, the prothrombin time of the hemophilia group was 90±12.2% before the start of the dosing and was 99.4±14.3% 12 weeks after the start of the dosing. The increase rate was 9.4±8.4%. The prothrombin time of the non-hemophilia group was 94.9±14.4% before the start of the dosing and was 100.0±16.8% 12 weeks after the start of the dosing. The increase rate was 5.4±12.6%. There was no significant difference in prothrombin time between the hemophilia group and the non-hemophilia group. The increased prothrombin time in both the hemophilia group and the non-hemophilia group suggests the increased coagulation activity of the coagulation factor VII and the other relevant coagulation factors.

Present invention claims priority based on Japanese Patent Application NO. 2006-053473 filed on Feb. 28, 2006 and the entire description is incorporated herein by reference.

Industrial Applicability

This invention is applied to manufacture of pharmaceutical composition for blood clotting disorder.

Sequence Listing Free Text

SEQ NO ID 1-6: primer

The invention claimed is:

1. A method of treating a blood clotting disorder comprising:
administering to a subject with the blood clotting disorder and without hepatitis C ribavirin or a pharmaceutically acceptable salt of ribavirin in an effective dose for treatment of the blood clotting disorder.

2. The method in accordance with claim 1, wherein ribavirin or the pharmaceutically acceptable salt of ribavirin is orally administered.

3. The method in accordance with claim 1, wherein the blood clotting disorder is a clotting factor deficiency.

4. The method in accordance with claim 1, wherein ribavirin or the pharmaceutically acceptable salt of ribavirin is administered in an effective dose for supplying an effective dose of a clotting factor VII in the subject.

5. The method in accordance with claim 4, wherein the clotting factor deficiency is at least either of hemophilia A and hemophilia B.

6. The method in accordance with claim 1, wherein ribavirin or the pharmaceutically acceptable salt of ribavirin is administered in an effective dose for preventing or treating hemorrhage or bleeding of the subject.

7. The method in accordance with claim 1, wherein the blood clotting disorder is clotting factor VII- involved blood clotting disorder.

8. The method in accordance with claim 1, the method including administration of ribavirin or the pharmaceutically acceptable salt of ribavirin in combination with an interferon.

9. The method in accordance with claim 8, wherein the subject has a viral infectious disease that is not HCV-induced.

10. The method in accordance with claim 9, wherein the viral infectious disease is an HIV-induced viral infectious disease.

11. A method of treating a clotting factor deficiency comprising:
administering to a subject with the clotting factor deficiency and without hepatitis C ribavirin or a pharmaceutically acceptable salt of ribavirin in an effective dose for treatment of the clotting factor deficiency.

12. The method in accordance with claim 11, wherein ribavirin or the pharmaceutically acceptable salt of ribavirin is administered in an effective dose for preventing or treating hemorrhage or bleeding of the subject.

13. The method in accordance with claim 11, wherein the clotting factor deficiency comprises at least one of hemophilia A and hemophilia B.

14. The method in accordance with claim 11, wherein the method includes administration of ribavirin or the pharmaceutically acceptable salt of ribavirin in combination with an interferon.

15. The method in accordance with claim 14, wherein the subject has a viral infectious disease that is not HCV-induced.

16. The method in accordance with claim 15, wherein the viral infectious disease is an HIV-induced viral infectious disease.

* * * * *